United States Patent
Szejnwald

(10) Patent No.: US 7,467,865 B2
(45) Date of Patent: Dec. 23, 2008

(54) ADJUSTABLE POLARIZED GOGGLES

(76) Inventor: Henryk Szejnwald, 1684 Fallenleaf La., Los Altos, CA (US) 94024

( * ) Notice: Subject to any disclaimer, the term of this patent is extended or adjusted under 35 U.S.C. 154(b) by 207 days.

(21) Appl. No.: 11/474,135

(22) Filed: Jun. 23, 2006

(65) Prior Publication Data

US 2007/0296912 A1    Dec. 27, 2007

(51) Int. Cl.
*G02C 7/12* (2006.01)
(52) U.S. Cl. .......................... 351/49; 351/158
(58) Field of Classification Search ................ 351/49, 351/44, 41, 158; 349/13
See application file for complete search history.

(56) References Cited

U.S. PATENT DOCUMENTS

| | | | |
|---|---|---|---|
| 2,005,426 A | 6/1935 | Land | |
| 2,813,459 A | 11/1957 | Archambault | |
| 3,944,346 A | 3/1976 | Shindler | |
| 4,119,369 A | 10/1978 | Eloranta et al. | |
| 4,149,780 A | 4/1979 | Young | |
| 4,386,832 A * | 6/1983 | Nannini | 351/49 |
| 4,943,152 A | 7/1990 | Whelen | |
| 5,355,183 A | 10/1994 | Andrea | |
| 5,790,225 A * | 8/1998 | Flados | 351/49 |
| 6,290,354 B1 * | 9/2001 | Safran | 351/57 |

* cited by examiner

*Primary Examiner*—Hung X Dang
(74) *Attorney, Agent, or Firm*—Michael Sherrard

(57) ABSTRACT

An adjustable polarized goggle provides for simple adjustment of the intensity of transmitted light with a mittened or gloved hand in a simple design having only three polarized elements. A continuous rounded common polarized element comprises the outer lens of the goggle and two coupled, rotatable, polarized elements inside the lens are disposed at an angle from one another to provide a compact shape conforming to the shape of a head. A foam liner traps an air volume between the polarized elements to reduce condensation.

10 Claims, 3 Drawing Sheets

ADJUSTABLE POLARIZED GOGGLES

FIELD OF THE INVENTION

This invention relates to adjustable-intensity polarized goggles or sunglasses.

BACKGROUND

Polarizers have been used to reduce glare and the light intensity in eyeglasses for some time. For example, U.S. Pat. No. 2,005,426 issued to Land in 1935 teaches adjustable polarized eyeglasses with two polarizer elements for each eye. The rear elements are rotatable so that the intensity of transmitted light can be adjusted.

U.S. Pat. No. 2,813,459 issued to Archambault in 1957 teaches adjustable polarized eyeglasses with two polarizer elements for each eye, wherein the rear elements are coupled so that the light intensity transmitted to both eyes is the same.

Further improvements are taught in U.S. Pat. No. 3,944,346 (Shindler), U.S. Pat. No. 4,119,369 (Eloranta et al), U.S. Pat. No. 4,149,780 (Young), U.S. Pat. No. 4,386,832 (Nannini), U.S. Pat. No. 4,943,152 (Whelen), and U.S. Pat. No. 5,355,183 (Andea).

SUMMARY OF THE INVENTION

Adjustable polarized goggles have a front-mounted slide controller to provide for simple adjustment of the intensity of transmitted light with a mittened or gloved hand. A simplified design requires only three polarized elements. A rounded polarized element of the goggles provides a common outer lens for both eyes and two coupled, rotatable, polarized elements inside the common outer lens are disposed at an angle from one another to provide a compact shape conforming to the shape of a head. A foam liner traps an air volume between the polarized elements to reduce condensation. The front-mounted slide controller is rounded to conform to the shape of the common outer lens and is coupled to the rotatable elements through apertures in the common outer lens to provide for easy adjustment of the transmitted light intensity.

As can be appreciated, the present invention provides a simplified construction in that only three polarized elements are required, as distinguished from four as in the typical prior art. Further, the present invention provides for a simplified and easy-to-use control mechanism that is easily adjusted with a mittened or gloved hand.

DETAILED DESCRIPTION

Figure 1:
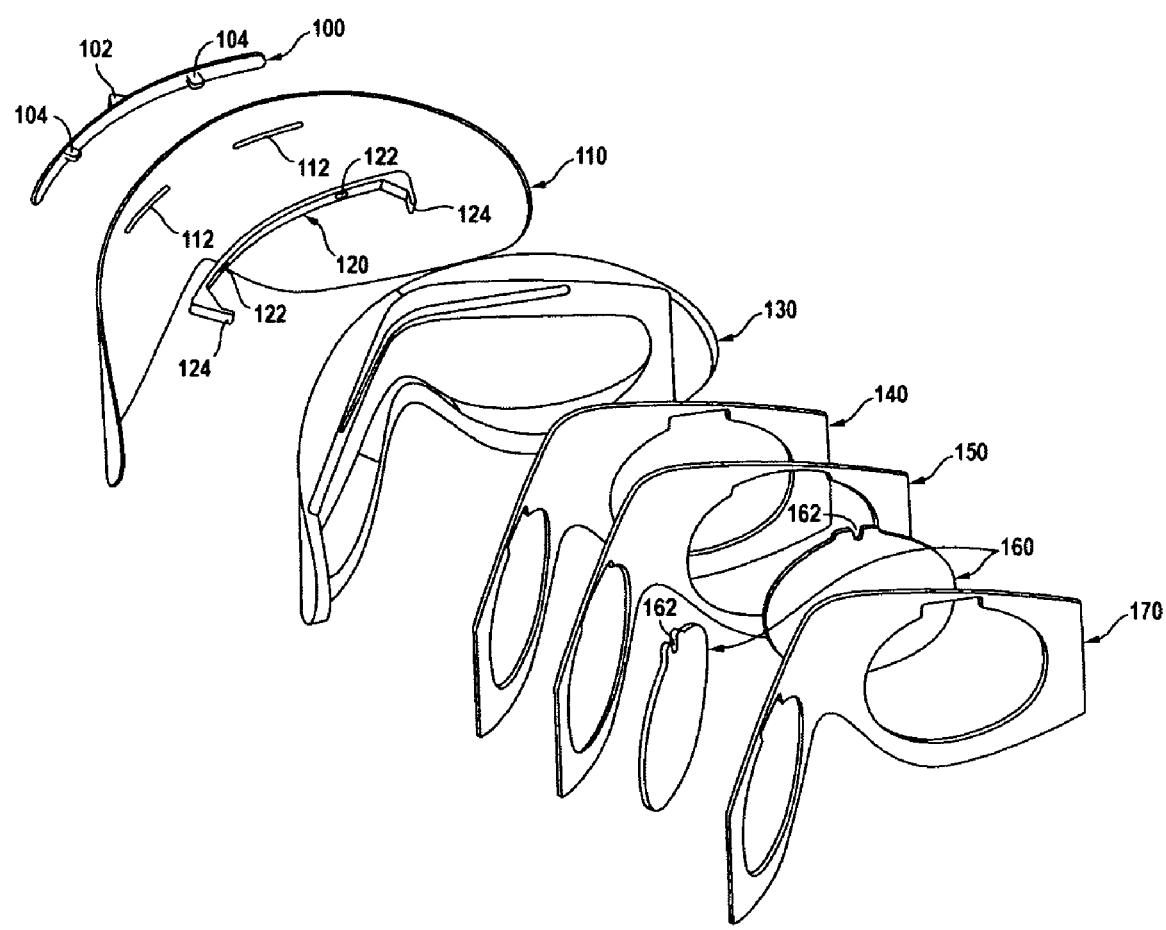
FIG. 1 is an exploded view of goggles in accordance with the preferred embodiment of the present invention.

An exploded view of goggles in accordance with the preferred embodiment of the present invention is illustrated in FIG. 1. A curved outside adjust tab 100 includes a protrusion 102 and two tabs 104. Protrusion 102 is shaped to be usable by a finger or thumb in a glove or mitten. Outside adjust tab 100 is molded round and mounted on the front of the goggles, which permits the top of the goggle to be used for unimpeded airflow.

Outer lens 110 is polarized and has a generally cylindrical shape adapted to conform to a face. It has a radius of approximately 5 inches, although this dimension may vary. Two horizontal slots 112 in outer lens 110 are adapted to receive tabs 104. Rounded inside adjust tab 120 includes two apertures 122 for fixedly receiving tabs 104 such that outside adjust tab 100 and inside adjust tab 120 move together and generally seal the horizontal slots 112 from moisture. Inside adjust tab 120 also includes inwardly directed control arms 124.

A foam liner 130 is form-fitted to the inside of outer lens 110 in a conventional manner to provide a substantial, but not complete, moisture barrier between the outside environment and the volume nearest the users eyes. Foam liner 130 fits between outer lens 110 and outside lens retainer 140 to substantially trap a volume of air at a temperature intermediate to the outside air and the face, thus reducing condensation on the lenses.

Outside lens retainer 140, lens spacer 150, and inside lens retainer 170 effectively sandwich two rotatable polarizer lenses 160, retaining them in place while allowing for their rotation. The two rotatable polarizer lenses 160 are mounted in positions significantly out-of-plane relative to one another. This angle is approximately 30 degrees in the illustrated preferred embodiment and preferably within a range of 15-45 degrees to provide a compact face-forming goggle. Control arms 124 protrude through a slot in foam liner 130 and through outside lens retainer 140 and engage in slots 162 of the rotatable polarizer lenses 160.

In operation, horizontal movement of outside adjust tab 100 moves inside adjust tab 120 and control arms 124. Control arms 124 engage slots 162 of rotatable polarizer lenses 160 and provide for rotation of rotatable polarizer lenses 160 and adjustment of the amount of light transmitted through the polarized elements 110 and 160.

Figure 2:
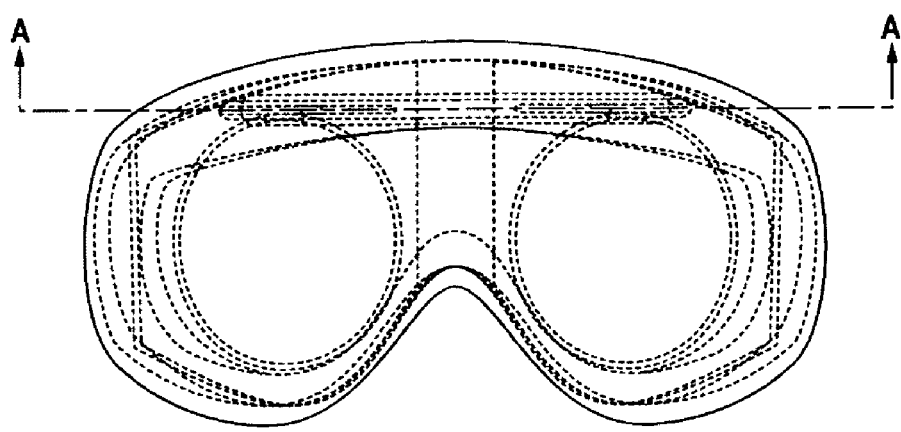
FIG. 2 provides a front view of the assembled goggles in accordance with the preferred embodiment of the present invention.
Figure 3:
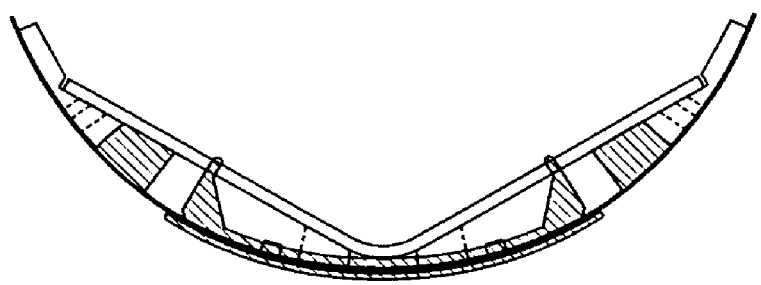
FIG. 3 provides a top view of goggles in accordance with the preferred embodiment of the present invention.
Figure 4:
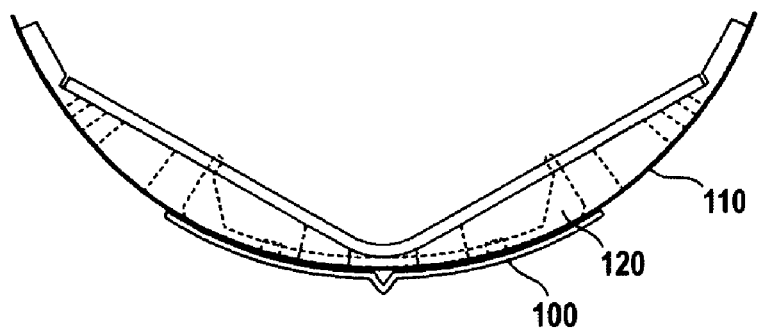
FIG. 4 shows a cutaway top view at the cross section "A-A" of FIG. 2.
Figure 5:
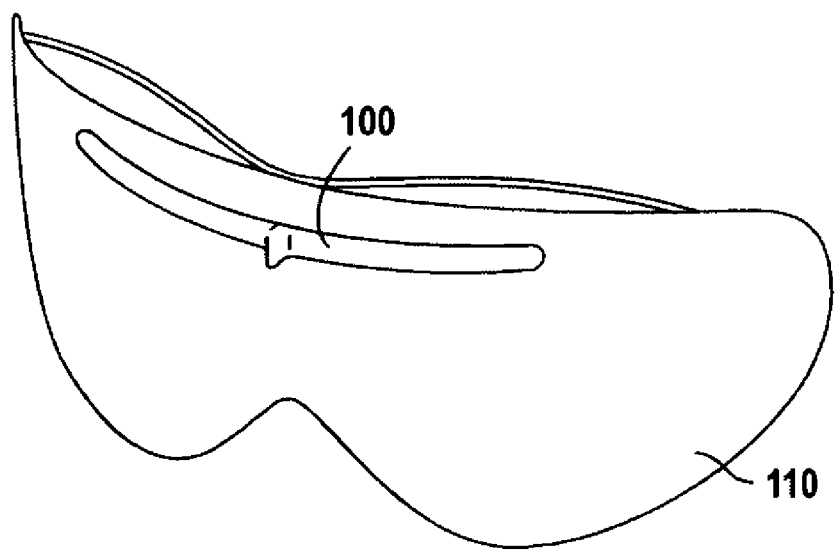
FIG. 5 provides a front perspective view of goggles in accordance with the preferred embodiment of the present invention.
Figure 6:
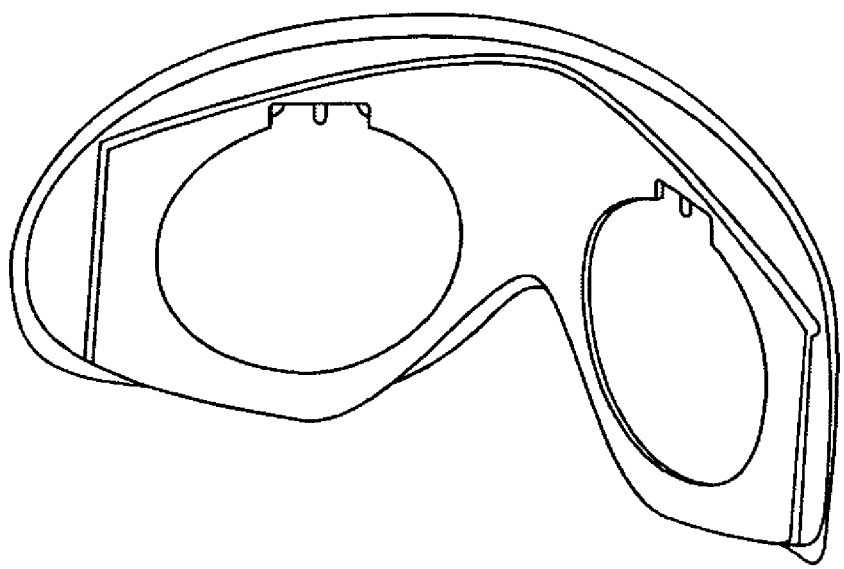
FIG. 6 shows a rear perspective view of goggles in accordance with the preferred embodiment of the present invention.

FIG. 2 provides a front view of assembled goggles in accordance with the preferred embodiment of the present invention and shows the location of a cross section "A-A." FIG. 3 provides a top view of the assembled goggles and FIG. 4 shows a cutaway top view at the cross section "A-A" of FIG. 2. FIG. 5 provides a front perspective view of the assembled goggles. FIG. 6 shows a rear perspective view of the assembled goggles. As can be appreciated, the rounded outer lens in combination with the out-of-plane mounting of the two rotatable lenses 160 provides a compact and face-fitting design.

The preferred embodiment of the present invention has been taught in the form of goggles such as used in the sport of skiing. However other types of eyewear or headwear could be adapted in accordance with the teachings herein. For example, the present invention can be readily adapted for use in helmets for racers and motorcycle riders. Alternatively, the device can be easily adapted for use in eyeglasses by eliminating the foam and adding side frame members. Further still, the invention could be incorporated in a lens or face-shield replacement for existing helmets or goggles. Accordingly, it is intended that the preceding detailed description not be limiting, but that the scope of the invention covers alterations and modifications that may fall within the scope of the following enumerated claims.

The invention claimed is:

1. Adjustable polarized eyewear comprising:
   a concave polarized lens adapted to encompass the field-of-view of both eyes of a wearer; and two rotatable polarizer elements, each element positioned within the concave polarized lens to encompass the field of view of one eye of the wearer.

2. Adjustable polarized eyewear as in claim 1 wherein the two rotatable polarizer elements are mounted significantly out-of-plane relative to one another.

3. Adjustable polarized eyewear as in claim 2 wherein the volume between the rounded polarized lens and the two rotatable polarizer elements is substantially enclosed to reduce airflow to and from the volume.

4. Adjustable polarized eyewear as in claim 2 wherein an elongated concave control piece is mounted to the exterior of the concave polarized lens and is adapted to control the rotation of both rotatable polarizer elements through at least one opening in the concave polarized lens.

5. Adjustable polarized goggles comprising a concave polarized lens adapted to encompass the field-of-view of both eyes of a wearer; two rotatable polarizer elements, each element positioned within the concave lens to encompass the field of view of one eye of the wearer; wherein the two rotatable polarizer elements are mounted significantly out-of-plane relative to one another; the volume between the rounded polarized lens and the two rotatable polarizer elements is substantially enclosed to reduce airflow to and from the volume; and an elongated concave control piece is mounted to the exterior of the concave polarized lens and is adapted to control the rotation of both rotatable polarizer elements through at least one opening in the concave polarized lens.

6. An adjustable polarized lens assembly comprising:
   a concave polarized lens adapted to encompass the field-of-view of both eyes of a wearer; and two rotatable polarizer elements, each element positioned within the concave polarized lens to encompass the field of view of one eye of the wearer.

7. An adjustable polarized lens assembly as in claim 6 wherein the two rotatable polarizer elements are mounted significantly out-of-plane relative to one another.

8. An adjustable polarized lens assembly as in claim 7 wherein the volume between the rounded polarized lens and the two rotatable polarizer elements is substantially enclosed to reduce airflow to and from the volume.

9. An adjustable polarized lens assembly as in claim 7 wherein an elongated concave control piece is mounted to the exterior of the rounded polarized lens and is adapted to control the rotation of both rotatable polarizer elements through at least one opening in the rounded lens.

10. Adjustable polarized ski goggles having a control on the front sized so as to be easily manipulated by a skier wearing gloves, the goggles comprising:
    a concave polarized lens adapted to encompass the field-of-view of both eyes of a wearer; and
    two rotatable polarizer elements, each element positioned within the concave lens to encompass the field-of-view of one eye of the wearer;
    both elements operatively coupled to the control.

* * * * *